United States Patent
Freson et al.

(10) Patent No.: US 9,645,058 B2
(45) Date of Patent: May 9, 2017

(54) SAMPLE ENCAPSULATION SYSTEM AND METHOD

(71) Applicant: ILLINOIS TOOL WORKS INC., Glenview, IL (US)

(72) Inventors: Lawrence L. Freson, Lake Bluff, IL (US); Kurt G. Adair, Lake Bluff, IL (US); Charles E. Shewey, Lake Bluff, IL (US); Douglas A. Ceckowski, Lake Bluff, IL (US); Sean O'Flaherty, Lake Bluff, IL (US); Anatoly Gosis, Palatine, IL (US); Yury Shkolnikov, Glenview, IL (US); Michael F. Hart, Mundelein, IL (US); Daniel P. Schmidt, Deerfield, IL (US)

(73) Assignee: ILLINOIS TOOL WORKS INC., Glenview, IL (US)

( * ) Notice: Subject to any disclaimer, the term of this patent is extended or adjusted under 35 U.S.C. 154(b) by 190 days.

(21) Appl. No.: 14/413,715

(22) PCT Filed: Jul. 16, 2013

(86) PCT No.: PCT/US2013/050703
§ 371 (c)(1),
(2) Date: Jan. 9, 2015

(87) PCT Pub. No.: WO2014/014925
PCT Pub. Date: Jan. 23, 2014

(65) Prior Publication Data
US 2015/0143928 A1   May 28, 2015

Related U.S. Application Data

(60) Provisional application No. 61/672,527, filed on Jul. 17, 2012.

(51) Int. Cl.
*G01N 1/22* (2006.01)
*G01N 1/36* (2006.01)
(Continued)

(52) U.S. Cl.
CPC ............... *G01N 1/36* (2013.01); *B30B 11/02* (2013.01); *B30B 11/04* (2013.01); *B30B 15/34* (2013.01);
(Continued)

(58) Field of Classification Search
USPC .............................................. 73/863, 863.11
See application file for complete search history.

(56) References Cited

U.S. PATENT DOCUMENTS

RE25,570 E * 5/1964 Lemelson ............. B21C 23/085
425/145
4,272,977 A * 6/1981 Gombas ............. B21D 51/2615
72/121
(Continued)

FOREIGN PATENT DOCUMENTS

CN 2482071 Y 3/2002
CN 1997495 A 7/2007
(Continued)

OTHER PUBLICATIONS

Office Action in European Application No. 13742565.8 dated May 19, 2016.
ISR for PCT/US2013/050703 mailed Apr. 9, 2014.

*Primary Examiner* — Clayton E Laballe
*Assistant Examiner* — Warren K Fenwick
(74) *Attorney, Agent, or Firm* — Levenfeld Pearlstein, LLC (57) ABSTRACT

A sample encapsulation system includes a base, a chamber having an inlet and a chamber housing in which the chamber is housed. The chamber is fixedly mounted at least in part
(Continued)

within the housing and the housing is movably mounted to the base. The system includes a cap, a first ram operably mounted to the cap for engaging the chamber inlet and a second ram positioned in the chamber opposite the inlet. The second ram is movable toward and away from the first ram. The chamber and housing are movable toward the cap for engaging the first ram with the chamber inlet during an encapsulation cycle and away from the cap, disengaging the first ram from the chamber inlet following an encapsulation cycle. The system includes heating and cooling assemblies and a temperature sensor located remotely from the chamber interior to automatically isolate cooling water to the system.

20 Claims, 9 Drawing Sheets

(51) Int. Cl.
  *B30B 11/02* (2006.01)
  *B30B 15/34* (2006.01)
  *B30B 11/04* (2006.01)
  *G01K 13/00* (2006.01)
(52) U.S. Cl.
  CPC ....... G01K 13/00 (2013.01); *G01N 2001/364* (2013.01)

(56) References Cited

U.S. PATENT DOCUMENTS

| | | | | |
|---|---|---|---|---|
| 4,834,917 | A | * | 5/1989 | Ramm ............... B09B 1/00 250/507.1 |
| 4,966,538 | A | | 10/1990 | Linke et al. |
| 5,841,038 | A | * | 11/1998 | Volz ................ B67B 7/24 73/863.85 |
| 6,315,936 | B1 | * | 11/2001 | Black ............... H01L 21/56 257/E21.502 |
| 7,404,707 | B2 | * | 7/2008 | Warren ............. G01N 1/286 425/128 |
| 2002/0022261 | A1 | * | 2/2002 | Anderson ......... B01F 11/0071 435/287.2 |
| 2003/0091676 | A1 | | 5/2003 | Warren et al. |
| 2008/0277825 | A1 | | 11/2008 | Venrooij |
| 2010/0218620 | A1 | * | 9/2010 | Hoyer ............. B01F 11/0014 73/863.11 |
| 2012/0111635 | A1 | * | 5/2012 | Caffell ............ E21B 10/02 175/58 |

FOREIGN PATENT DOCUMENTS

| | | |
|---|---|---|
| CN | 202256018 U | 5/2012 |
| JP | 5730717 U | 2/1982 |
| JP | S5820919 Y2 | 5/1983 |
| JP | 2010094721 A | 4/2010 |

* cited by examiner

SAMPLE ENCAPSULATION SYSTEM AND METHOD

RELATED APPLICATIONS

The present application is a National Phase of International Application Number PCT/US2013/050703 filed Jul. 16, 2013 and claims priority of U.S. Provisional Application No. 61/672,527 filed Jul. 17, 2012.

BACKGROUND

The examination of samples, such as by metallographic examination, requires a number of preparatory steps. For example, a sample may need to be cut or sectioned to a specific size, mounted or encapsulated in a supporting material and ground and/or polished for examination. Such samples are mounted to facilitate handling and to maintain the ability to distinguish between the sample and the material in which the sample is mounted. Mounting materials are typically resins, such as thermoset or thermoplastic resins, including phenolics, phthalates, epoxies, methacrylates and the like. Such materials are commercially available from Buehler, an ITW Company, of Lake Bluff, Ill.

Mounting can be carried out in a number of ways. One way in which to mount a sample is a compression mounting process. In a compression mounting process, the sample is placed in a chamber or mold along with the mounting compound. The sample and compound are heated under pressure for example, by use of heating coils and a hydraulic ram. After a predetermined period of time at a set temperature and pressure, the heat source is isolated from the mold, and a cooling fluid is circulated around the mold to cool the encapsulated sample. After a predetermined period of time, the pressure is released and the sample is removed from the mold.

If the encapsulated sample (i.e., the sample and the molding compound) is not sufficiently cooled prior to releasing pressure and removal from the mold, the molding compound may change shape or shrink (for example, pull away from the sample). This can result in abrasive rounding the edges of the sample during later sample preparation steps, such as grinding, which may compromise the later metallographic examination. In addition, it may be difficult to handle the encapsulated sample if it is not sufficiently cooled.

To prevent premature removal of the sample, in a typical operation, the cooling system is operated for a set period of time. This time is used regardless of whether the sample has already reached a desired final temperature. As such, and as often occurs, the cooling system is run too long and the cooling liquid, usually water from a municipal water system, is wasted.

In a compression mold system, the mold that is used, as stated above, is maintained under high pressure at a high temperature. It is not unusual for the mold to reach pressures as high as 4000 psi. within the mold or pressure chamber. In a conventional system, the sample and material are positioned in the mold and a cap is positioned on an upper end of the mold. A hydraulic ram is moved into the chamber to exert a force on the sample and material, and heating coils are actuated to heat the chamber with the material and sample. The chamber is a straight-walled cylindrical chamber and the cap includes a plug that, once the cap is locked in place, inserts into the top of the chamber. The plug fits tightly into the chamber to assure that the pressure boundary within the chamber is maintained.

One drawback to this configuration is that the plug that inserts into the top of the chamber can be difficult to insert due to the tight tolerances, and the cap may be difficult to secure or lock onto the chamber. It may also be difficult to loosen and remove the cap as the plug fits tightly in the chamber top.

In that such systems operate at high temperatures and pressures, the closure systems, that is the caps that fit onto the mold or pressure chamber are quite heavy, as they are typically fabricated from steel. In addition, the caps are mounted to the system so as to remain attached to the system. As such, the caps can be difficult to maneuver and can require considerable force (or user strength) to manipulate.

Accordingly, there is a need for a sample preparation or encapsulation system having a mold chamber that readily permits closing and locking as well as unlocking and opening the chamber cap without undue exertion by an operator. Desirably, such a system also includes cap assembly that permits readily opening and closing the system without undue force or user strength. More desirably still, such a system includes an automated cooling system that terminates water flow at a specified time, once the sample has been determined to have reached a desired final temperature.

SUMMARY

A sample encapsulation system includes a base, a chamber having an inlet and a chamber housing in which the chamber is housed. The chamber is fixedly mounted at least in part within the chamber housing and the chamber housing is movably mounted to the base.

The system includes a cap, a first ram operably mounted to the cap for engaging the chamber inlet and a second ram positioned in the chamber opposite the inlet. The second ram is movable toward and away from the first ram.

The chamber and housing are movable toward the cap for engaging the first ram with the chamber inlet during an encapsulation cycle and away from the cap, disengaging the first ram from the chamber inlet following an encapsulation cycle.

In an embodiment, the cap can be formed as part of a cap assembly, in which the cap assembly includes a mounting plate, and the cap secures to mounting plate. The mounting plate is stationary relative to the housing and chamber. When the cap is secured to the mounting plate, the chamber and housing are movable toward the mounting plate for the first ram to engage the chamber inlet. The chamber and housing are movable away from the mounting plate to disengage the first ram from the chamber inlet.

The chamber can have a tapered wall section at about the inlet that expands outwardly toward the inlet. In such an arrangement, the first ram has a tapered profile for mating with the chamber inlet tapered wall. In an embodiment, the chamber inlet can be configured with a two-step tapered wall section. A first tapered wall section at the inlet transitions to a relatively straight-walled section that transitions to a second tapered wall section. The first ram can have a tapered wall for mating with the chamber second tapered wall section during the encapsulation cycle and for disengaging from the second tapered wall section following the encapsulation cycle.

In an embodiment, the chamber and/or chamber housing includes an inwardly oriented lip at a lower end thereof. The second ram engages the inwardly oriented lip following the encapsulation cycle to move the chamber and chamber housing away from the cap and to disengage the chamber inlet from the first ram. Disengaging the second ram from the inwardly oriented lip permits movement of the chamber housing and chamber toward the cap for engaging the chamber inlet with the first ram.

The cap can be movable toward and away from the mounting plate and can be locked to the mounting plate when in the encapsulation cycle. The cap is movable toward and away from the mounting plate along a post. A constant force spring can be operably connected to the cap for moving the cap toward and away from the mounting plate.

In an embodiment, the sample encapsulation system includes a base, a chamber and a chamber housing in which the chamber is housed. The chamber is fixedly mounted at least in part within the chamber housing and the chamber housing is movably mounted to the base. The system includes a cap.

A heating assembly and a cooling assembly are disposed about the chamber and a temperature sensor is mounted remotely from an interior of the chamber. The temperature sensor can be mounted to the chamber housing remote from an encapsulated sample within the chamber. The remote sensed temperature is used to continue or stop operation of the cooling system following a predetermined period of time after the remote sensed temperature reaches a set point temperature based upon a predicted temperature of the encapsulated sample as determined by the remote sensed temperature.

The system can include means for determining the predetermined period of time of cooling system operation. One such predetermined period of time is a time lag ($\Delta t$). For an encapsulated sample having a predetermined diameter $\Delta t$ is determined according to the formula $\Delta t = A + BT + Ct$, where T is a hold temperature of the encapsulated sample in degrees C., t is a hold time in seconds at the hold temperature of the encapsulated sample and where A, B and C are experimentally determined factors based upon the set point temperature.

In one embodiment, for an encapsulated sample having a 1.0 to 1.25 inch diameter and a set point temperature of 40 degrees C., A is 6.73, B is 0.0783 and C is −0.0115 or at a set point temperature of 55 degrees C. A is −8.12, B is 0.130 and C is 0.00625t, or for an encapsulated sample having a 1.5 inch diameter and a set point temperature of 40 degrees C., A is 1.8, B is 0.320 and C is 0.604, or at a set point temperature of 55 degrees C., A is −29.0, C B is 0.367 and C is +0.0688t, or for an encapsulated sample having a 2.0 inch diameter and a set point temperature 40 degrees C., A is 1.125, B is 0.430T and C is 0.156t, or at a set point temperature of 55 degrees C., A is −52.9, B is 0.543 and C is 0.162.

The system can further include means for establishing the set point temperature, means for determining the lag time ($\Delta t$) for cooling fluid flow and means for stopping fluid cooling flow after the set point temperature has been reached and the lag time has expired. One such means for determining the lag time ($\Delta t$) for cooling fluid flow is based, at least in part, on a size of the sample and the set point temperature. One such means for determining the lag time ($\Delta t$) for cooling fluid flow is based, at least in part, on a diameter of the sample.

These and other features and advantages of the present disclosure will be apparent from the following detailed description, in conjunction with the appended claims.

BRIEF DESCRIPTION OF THE DRAWINGS

The benefits and advantages of the present invention will become more readily apparent to those of ordinary skill in the relevant art after reviewing the following detailed description and accompanying and drawings, wherein.

DETAILED DESCRIPTION

While the present invention is susceptible of embodiment in various forms, there is shown in the drawings and will hereinafter be described a presently preferred embodiment with the understanding that the present disclosure is to be considered an exemplification of the device and is not intended to be limited to the specific embodiment illustrated.

Figure 1:
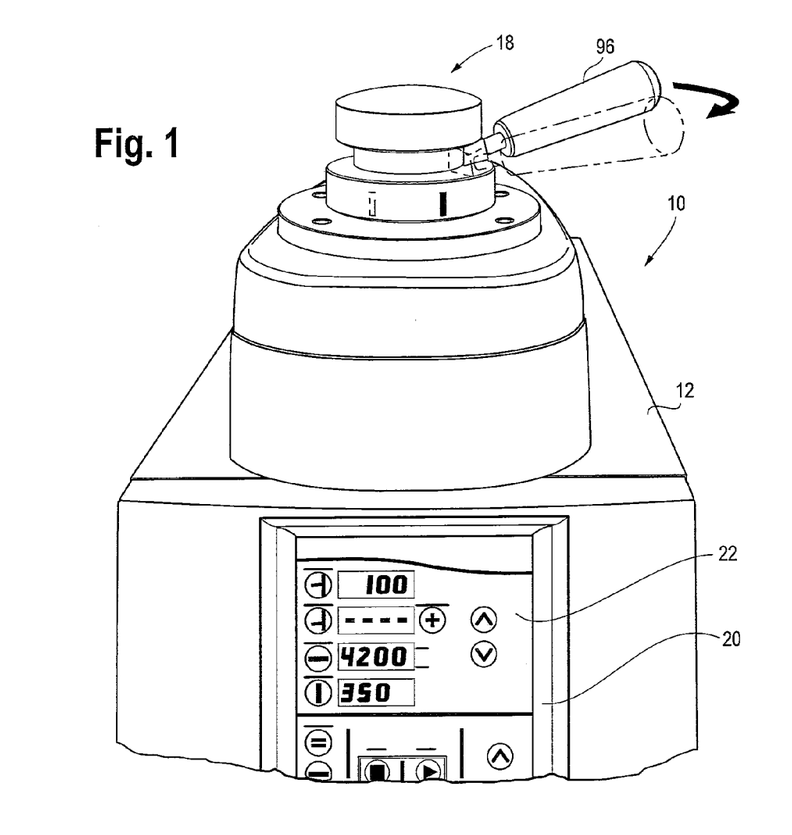
FIG. 1 is a perspective illustration of a sample preparation system with the chamber cap handle rotated to the open position and shown, in phantom in the locked position.
Figure 2:
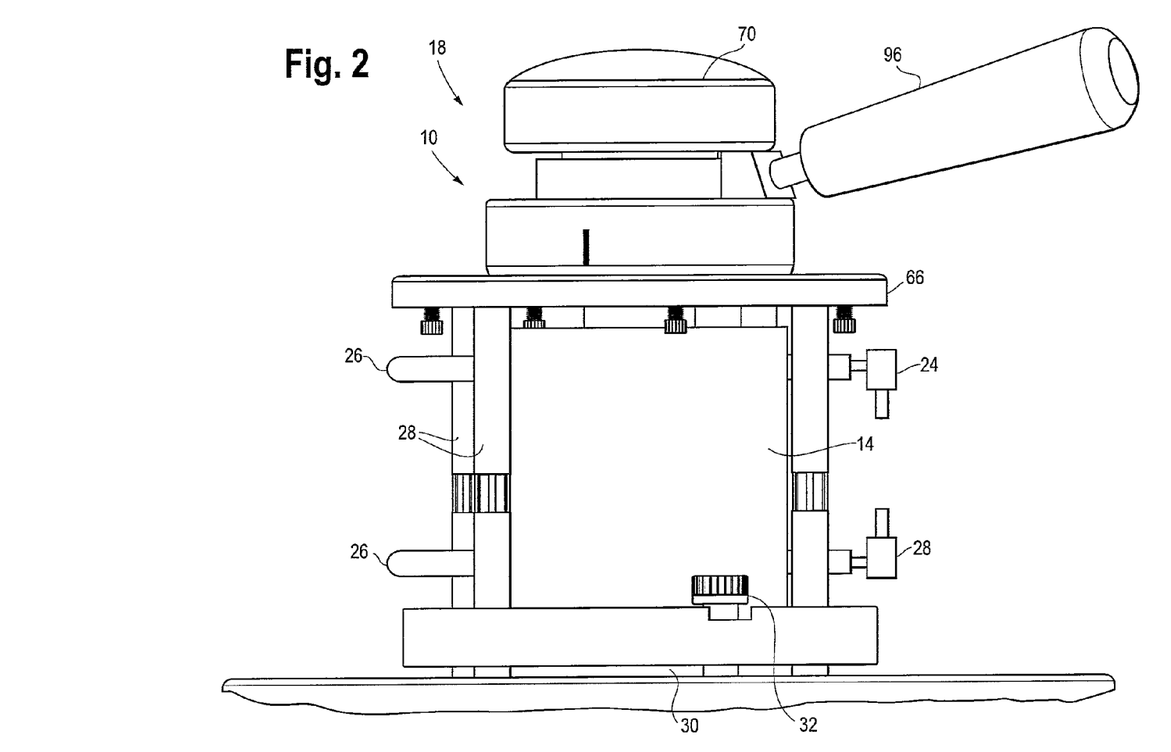
FIG. 2 is a front view illustration of the chamber portion of the system.
Figure 3:
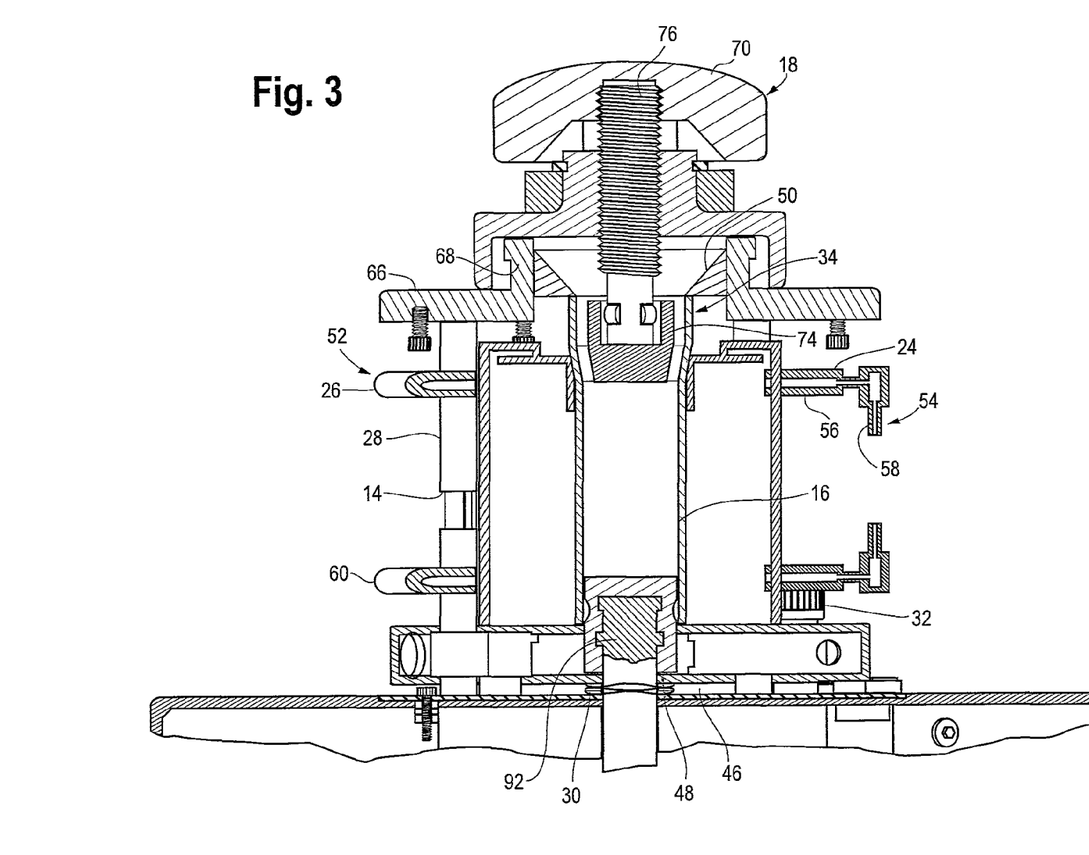
FIG. 3 is a partially cut-away view of the chamber portion.

Referring now to the figures and in particular, to FIGS. 1-3, there is shown generally a sample preparation or encapsulation system 10. The system 10 includes, generally, a base 12 having a chamber housing 14 with a chamber 16, a chamber cap assembly 18 and a control system 20.

The base 12 is a mounting system for the chamber housing 14, chamber 16, cap assembly 18 and control system 20, and encloses these components. A control panel 22 is mounted on the base 12. Electrical 24 and fluid 26 connectors extend into the base 12 and connect to the various components within the base 12.

The chamber 16 is fixedly mounted within the chamber housing 14. The housing 14 is mounted to the base 12 by columns or posts 28 and is moveable along the posts 28 toward and away from the base 12. As such, as the housing 14 moves toward and away from the base 12, the chamber 16 likewise moves toward and away from the base 12. A biasing element 30, such as the illustrated wave springs (Belleville washers) bias the chamber housing 14 away from the base 12. A stop 32, such as the illustrated shoulder screw, permits setting the distance from which the housing 14 can move away from the base 12. The shoulder screw 32 height (distance from the base 12) can be adjustable.

Figure 4:
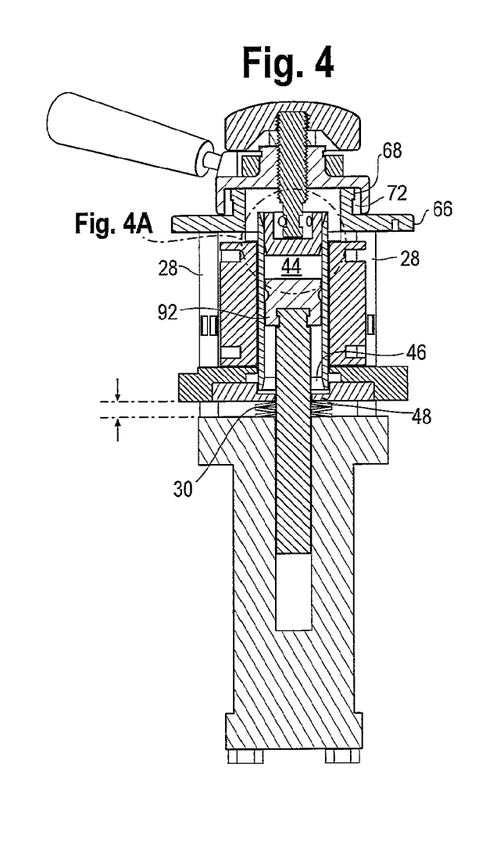
FIG. 4 is a partial cross-sectional view of the chamber shown in the locked position.
Figure 4A:
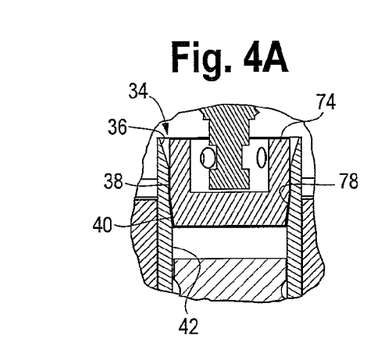
FIG. 4A is a partial sectional view of the plug when the chamber is locked.
Figure 5:
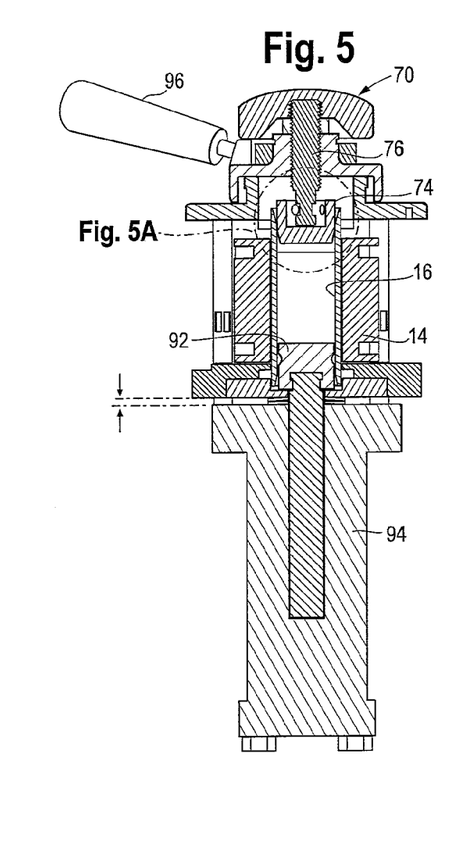
FIG. 5 is a partial cross-sectional view of the chamber shown in the unlocked position.
Figure 5A:
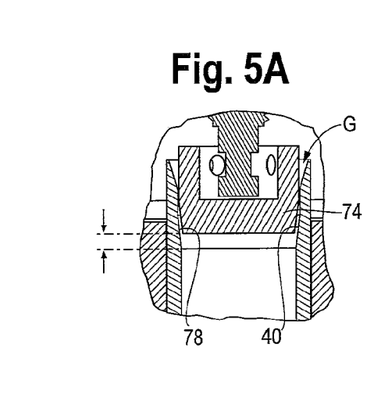
FIG. 5A is a partial sectional view of the plug when the chamber is unlocked.
Figure 6:
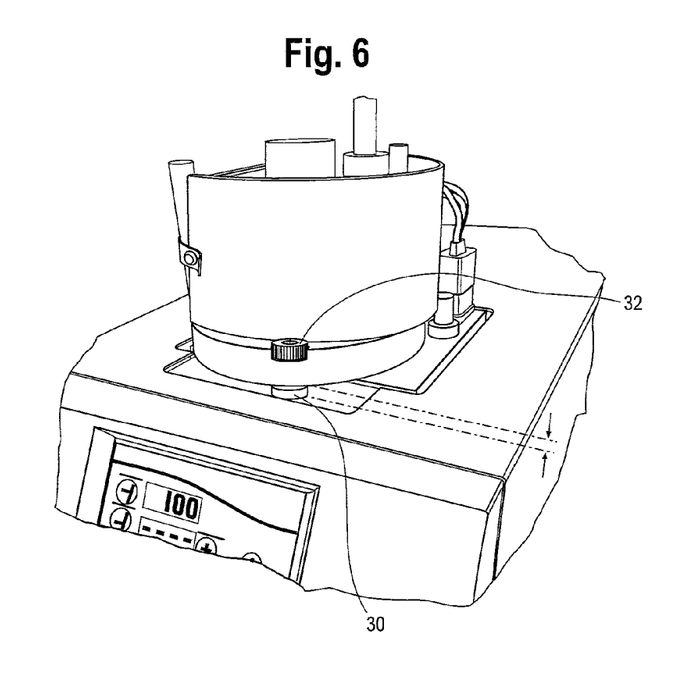
FIG. 6 illustrates the lower part of the chamber when the chamber is in the unlocked position, showing no gap between the lower portion and spacers at the base.
Figure 7:
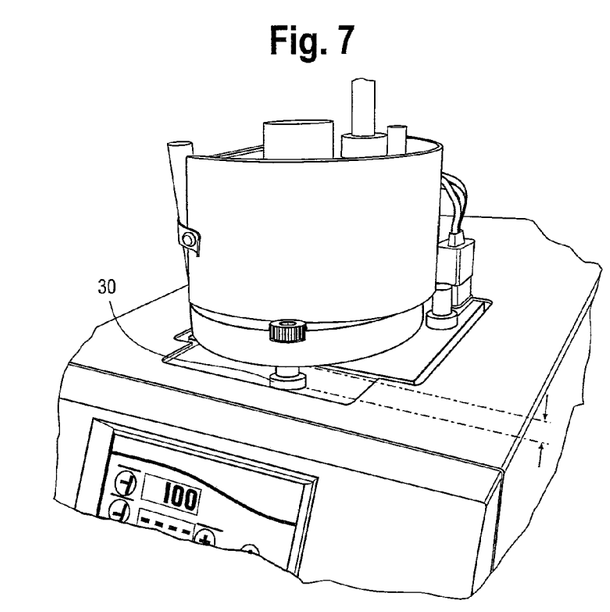
FIG. 7 is an illustration similar to FIG. 6, showing the lower part of the chamber when the chamber is in the locked position, showing the gap between the lower portion and spacers at the base.

The chamber 16 has a tapered or angled inlet as indicated at 34 (see FIGS. 4A and 5A). In a present embodiment, the inlet 34 has a two-step taper. A first or outer tapered wall section 36 at the immediate inlet 34 transitions to a straight-walled section 38, which transitions to a second or inner tapered wall section 40, which then transitions to another straight walled section 42 that defines the mold cavity 44. In a present embodiment, the walls 36, 40 are tapered at an angle of about 7 degrees. An opposite end 46 of the chamber 16 includes an inwardly directed lip 48. A fill guide 50 (see, FIG. 3) is positioned at about the chamber inlet 34 to assist filling the chamber 16 with resin or other encapsulating material, which may be provided in granulated or powdered form.

The chamber housing 14 includes both a cooling system 52 and a heating system 54. The heating system 54 includes one or more heating coils 56 within the chamber housing 14, surrounding the chamber 16. In a present embodiment, the heating coils, are electric heating coils, that are positioned around the chamber 16. Contacts or connectors 58 provide for connecting power to the heating coils 56. The cooling system 52 includes cooling coils 60, such as liquid cooled coils that are positioned around within chamber housing 14, surrounding the chamber 16. One or more inlets and outlets 62 are positioned about the chamber housing 14 for supplying liquid to and carrying liquid from the coils 60. A present system uses a water cooled system.

One or more temperature sensors 64 are positioned on the chamber housing 14, outside of the pressure boundary, that is outside of the chamber 16, to sense the temperature of the housing 14.

The cap assembly 18 includes a cap mounting plate 66 disposed at an end of the chamber 16 opposite the base 12. The mounting plate 66 can be mounted to, for example, an upper end of the posts 28. The mounting plate 66 is fixed relative to the base 12. In this configuration, the chamber housing 14 (and chamber 16) move toward and away from the mounting plate 66 or move between the base 12 and the mounting plate 66.

The mounting plate 66 includes a securing assembly 68, such as the illustrated bayonet mount, to secure a cap 70 to the mounting plate 66. The cap 70 includes a cooperating securing assembly 72, such as the illustrated mating bayonet, to secure the cap 70 to the mounting plate 66. It will be understood that in this configuration, the cap 70 remains fixed to the mounting plate 66 which is stationary relative to the moving chamber housing 14 and chamber 16. It will also be understood that any type of mount can be used to secure the cap 70 to the mounting plate 66 and that the bayonet mount is illustrative of one type of mount that can be used.

The cap 70 includes a first or upper ram 74 mounted thereto. The upper ram 74 is configured for insertion into the chamber 16 at the inlet 34 to establish a pressure boundary and forms one side or end of the mold cavity 44. The upper ram 74 is mounted to the cap 70 by an adjustable element 76, such as the illustrated threaded rod to allow for properly adjusting the seating of the upper ram 74 in the chamber 16.

The upper ram 74 has a tapered wall 78 that mates with the chamber second tapered wall section 40. Accordingly, in a present embodiment, the upper ram tapered wall 78 has a taper of about 7 degrees.

Figure 8:
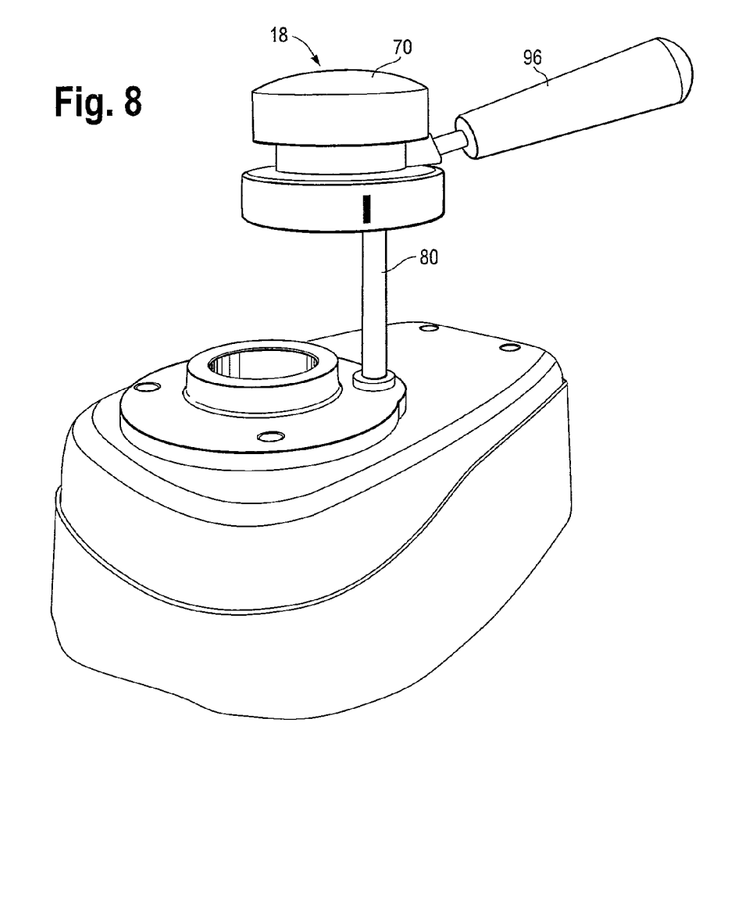
FIG. 8 is an illustration of the chamber cap mounting to the base.
Figure 9:
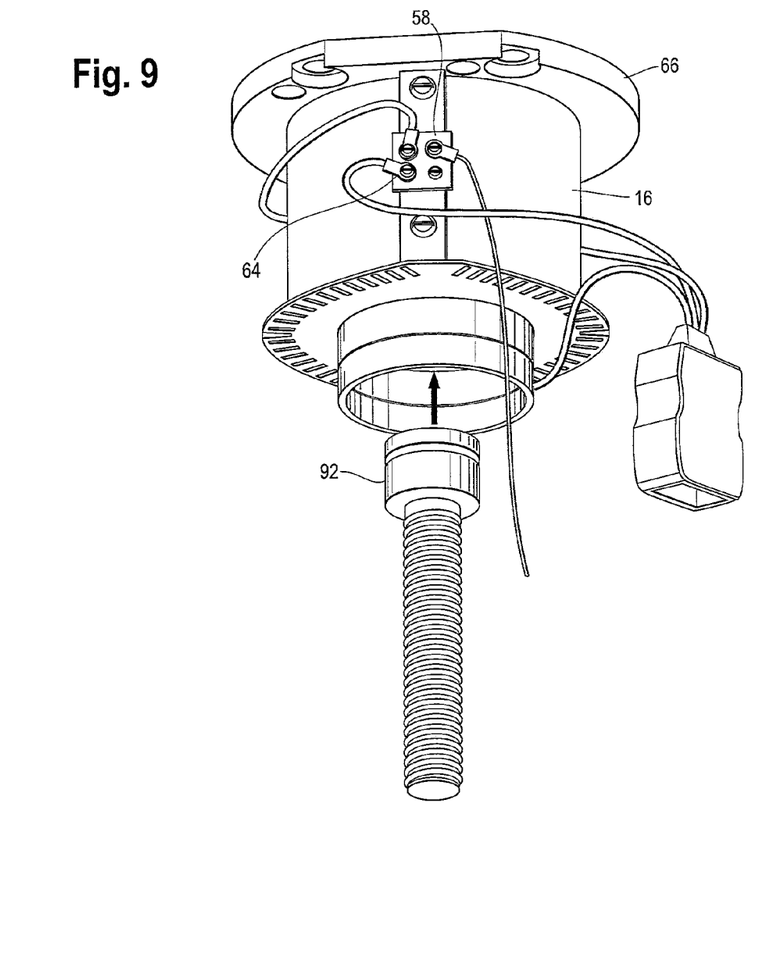
FIG. 9 is an illustration of the lower part of the chamber housing showing the lower ram and various electrical and fluid connections to the housing.
Figure 10:
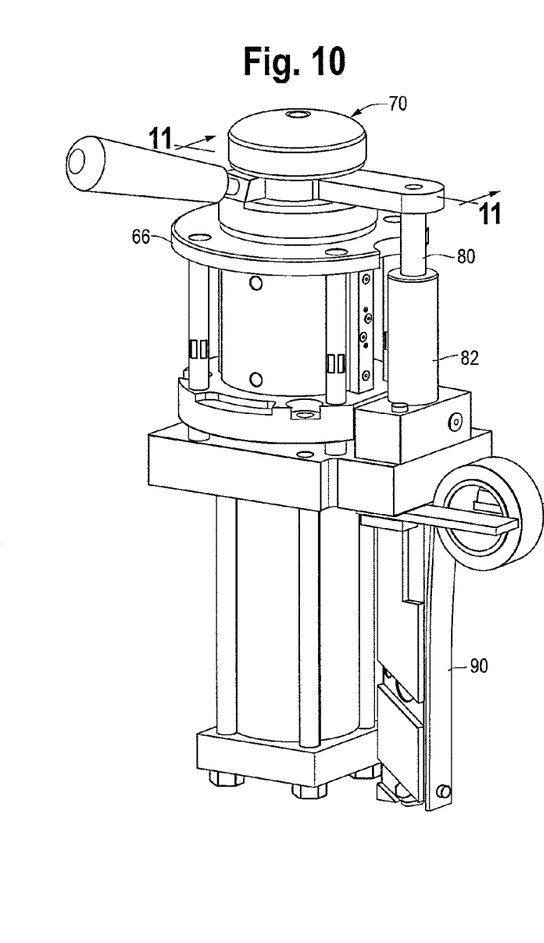
FIG. 10 is a perspective illustration of the housing, chamber cap and constant force spring mounting of the cap to the base.
Figure 11:
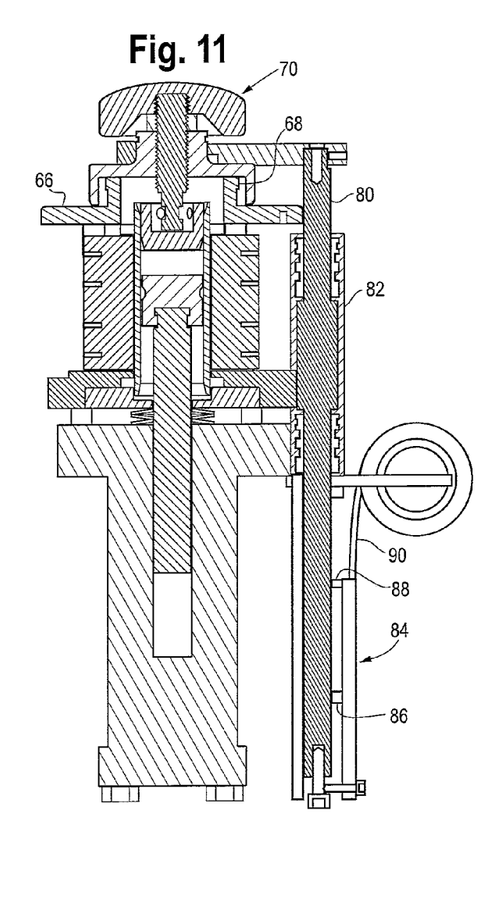
FIG. 11 is a cross-sectional view of the housing, chamber cap and constant force spring mounting of the cap to the base.

Referring to FIGS. 8, 10 and 11, the cap 70 is mounted to the base 12 by a post 80 that rides in a linear bearing 82 that, when the cap 70 is in the unlocked position, allows the cap 70 to be lowered and raised toward and away from the mounting plate 66. The post 80 includes a cam lock arrangement 84 which permits the cap 70 to be held or maintained in the open position when fully retracted. In a present system, the cam lock 84 is configured as a pin 86 that engages a shoulder 88 on the housing 12. In this manner, the cap 70 can be unlocked from the mounting plate 66 and raised, away from the plate 66, to allow access to the chamber 16. By rotating the cap 70 and post 80, the cap 70 can be held in place in the open position with the pin 86 resting on the shoulder 88. By rotating the cap 70 and post 80 in the opposite direction (so as to align with the chamber 16), the pin 86 can be disengaged from the shoulder 88 and the cap 70 lowered onto the plate 66. A constant force spring 90, such as the illustrated wound steel spring, facilitates raising and lowering the cap 70 with minimal force. The spring 90 has a force about equal to the weight of the cap 70.

The system 10 includes a lower ram 92 disposed in the chamber 16, opposite the upper ram 74. In a present embodiment, the lower ram 92 is a hydraulic ram that is driven by a cylinder 94, and moves upward toward the upper ram 74 when in the molding or encapsulation cycle, and downward, away from the upper ram 74 for loading the chamber 16 and when releasing an encapsulated sample.

In use, the cap 70 is opened and fully retracted. The cap 70 is then rotated with the post 80 so that the cap 70 is held open by the pin 86 resting on the shoulder 88. At this point in time, the lower ram 92 is in the withdrawn position. When in the withdrawn position, the lower ram 92 engages the lip 48 at the bottom of the chamber 16 and draws the chamber 16 and chamber housing 14 downward, away from the cap mounting plate 66 and toward the base 12.

A sample and encapsulating material are introduced into the chamber 16. The cap 70 and post 80 are then rotated to disengage the pin 86 from the shoulder 88 and the cap 70 is lowered onto the mounting plate 66. The cap 70 is then locked to the mounting plate 66 by rotating the handle 96 to engage the mating bayonet elements 68, 72. The upper ram 74 is positioned in, but not fully engaged with the chamber inlet end 34 (see FIG. 5A).

The encapsulation cycle commences with the cylinder 94 actuating and the lower ram 92 moving up. As the lower ram 92 comes off of the lip 48, the spring 30 that engages the chamber 16 and housing 14 urges the chamber housing 14 upward and moves the chamber inlet 34 fully into engagement with the upper ram 74 (see FIG. 4A). The upper ram taper 78 and the chamber second or inner tapered wall section 40 seal the ram 74 in the chamber 16. Force up to about 12,000 pounds is exerted by the lower ram 92 moving into the chamber 16, toward the upper ram 74.

Heat is then applied to the chamber 16 by the heating system 54, and the heat and pressure exerted by the lower ram 92 against the sample and encapsulation material, over a predetermined period of time, fuses the encapsulation material and the sample to form the encapsulated sample.

Following expiration of the predetermined period of time, the heating system 54 isolates and the cooling system 52 commences cooling of the sample. After reaching a predetermined temperature, the lower ram 92 withdraws or retracts. As the ram 92 retracts, it engages the lip 48, which pulls or urges the chamber 16 and chamber housing 14 downward, toward the base 12 and away from the upper ram 74. As the chamber 16 moves away from the upper ram 74, the gap G formed between the upper ram 74 and the chamber second tapered wall section 40 facilitates more easily loosening the cap 70 from the mounting plate 66. That is, by moving the upper ram 74 out of contact with the inner wall of the chamber inlet 34, the cap 70 is readily removed from the chamber 16 and the cap 70 can be opened and the encapsulated sample removed.

As set forth above, the sample must be sufficiently cooled to permit handling, to ensure edge retention and to minimize any shrinking that may otherwise occur, so as to maintain the integrity of the sample. Prior known sample preparation systems use a timed system to cool the sample. That is, cooling water was run through the system for a predetermined period of time regardless of whether the desired temperature was reached. It will be appreciated that it is difficult, at best, to directly monitor or measure the temperature of the sample during the cooling step. Thus, if the desired temperature was not achieved and the sample was too hot, it may lack integrity and may be difficult to handle. Conversely, if the cooling system ran too long, then cooling water was wasted.

The present sample encapsulation system 10 uses a novel system in which a remotely measured temperature is sensed and, based upon the measured temperature, the time at which the encapsulated sample will reach a desired temperature is determined. This provides a higher degree of assurance that the sample has been cooled to a temperature that allows comfortable handling and provides a high degree of encapsulated sample integrity.

In a present system, cooling liquid flow, in the present embodiment, cooling water flow, is controlled based upon the remotely measured temperature in conjunction with empirically derived relations. The temperature of the housing 14, outside the pressure boundary or chamber 16, is measured by a temperature sensing device 64, such as a thermocouple, a thermistor, a resistance temperature detector (RTD), an infrared sensor or the like. A present system uses a RTD that is mounted to the chamber housing 14 to measure the temperature of the outer surface of the chamber housing.

Testing was conducted to determine the time profiles to a comfortable handling temperature for various samples of encapsulated samples, after the housing temperature had reached a predetermined temperature. Four different sizes (diameters) of samples were tested: 1.0 inch, 1.25 inches, 1.5 inches and 2.0 inches. The samples all consisted of ½ inch diameter steel balls encapsulated in resin. Each of the samples was heated to a predetermined temperature (T in degrees C.) and held at that temperature for a predetermined period of time (t in seconds). The time lag ($\Delta t$ in seconds) between when the housing reached a target temperature $T_t$ of 40 degrees C. (104° F.) and the sample reached the target temperature $T_t$ of 40 degrees C. was then measured. The data is provided in Table 1, below.

TABLE 1

TEST DATE FOR VARIOUS SAMPLE SIZES AT VARYING HOLD TEMPERATURES AND HOLD TIMES AND SAMPLE TO HOUSING COOLING LAG TIMES

| Sample No. | Mold size (in.) | Hold Temp (° C.) | Hold Time (sec) | Time Diff - $\Delta t$ (sec) |
|---|---|---|---|---|
| 1 | 1.00 | 100 (212° F.) | 60 | 12 |
| 2 | 1.00 | 100 | 180 | 15 |
| 3 | 1.00 | 100 | 300 | 12 |
| 4 | 1.00 | 200 (392° F.) | 60 | 27 |
| 5 | 1.00 | 200 | 180 | 25 |
| 6 | 1.00 | 200 | 300 | 18 |
| 7 | 1.25 | 100 | 60 | 9 |
| 8 | 1.25 | 100 | 180 | 12 |
| 9 | 1.25 | 100 | 300 | 15 |

TABLE 1-continued

TEST DATE FOR VARIOUS SAMPLE SIZES AT VARYING HOLD TEMPERATURES AND HOLD TIMES AND SAMPLE TO HOUSING COOLING LAG TIMES

| Sample No. | Mold size (in.) | Hold Temp (° C.) | Hold Time (sec) | Time Diff - $\Delta t$ (sec) |
|---|---|---|---|---|
| 10 | 1.25 | 200 | 60 | 21 |
| 11 | 1.25 | 200 | 180 | 18 |
| 12 | 1.25 | 200 | 300 | 13 |
| 13 | 1.50 | 100 | 60 | 49 |
| 14 | 1.50 | 100 | 180 | 39 |
| 15 | 1.50 | 100 | 300 | 46 |
| 16 | 1.50 | 200 | 60 | 58 |
| 17 | 1.50 | 200 | 180 | 82 |
| 18 | 1.50 | 200 | 300 | 90 |
| 19 | 2.00 | 100 | 60 | 40 |
| 20 | 2.00 | 100 | 180 | 73 |
| 21 | 2.00 | 100 | 300 | 88 |
| 22 | 2.00 | 200 | 60 | 97 |
| 23 | 2.00 | 200 | 180 | 109 |
| 24 | 2.00 | 200 | 300 | 133 |

In testing, it was found that changes in coolant (water) flow rate did not significantly impact $\Delta t$, so long as the flow rate was between about 0.8 liters per minute (0.8 l/min or 0.21 gal/min) and 1.9 l/min (0.50 gal/min). In addition, it was also found that changes in coolant inlet temperature did not significantly impact $\Delta t$, so long as coolant inlet temperature was between about 17 degrees C. (62.6° F.) and 25 degrees C. (77° F.).

The data was then plotted and algorithms were developed for each of the sample sizes (diameters). It was found that the algorithms for the 1.00 inch and 1.25 inch samples were the same (Eq. 1). The algorithms for the 1.50 and 2.00 inch diameter samples were different from the small sample algorithm and from each other (Eq. 2—1.50 inch sample; Eq. 3—2.00 inch sample).

For the 1.00 and 1.25 inch diameter samples, it was found that the time lag or $\Delta t$ between when the housing reached a target temperature $T_t$ of 40 degrees C. (104° F.) and the sample reached the target temperature $T_t$ of 40 degrees C. is defined by:

$$\Delta t = 6.73 + 0.0783T - 0.0115t, \quad \text{(Eq. 1)}$$

Where $\Delta t$ is the lag time in seconds, T is the hold temperature of the sample in degrees C. and t is the hold time in seconds at temperature T of the sample.

For the 1.50 inch diameter sample, it was found that the time lag or $\Delta t$ between when the housing reached a target temperature $T_t$ of 40 degrees C. and the sample reached he target temperature $T_t$ of 40 degrees C. is defined by:

$$\Delta t = 1.8 + 0.320T + 0.604t, \quad \text{(Eq. 2)}$$

Again, where $\Delta t$ is the lag time in seconds, T is the hold temperature of the sample in degrees C. and t is the hold time in seconds at temperature T of the sample.

For the 2.00 inch diameter sample, it was found that the time lag or $\Delta t$ between when the housing reached a target temperature $T_t$ of 40 degrees C. and the sample reached the target temperature $T_t$ of 40 degrees C. is defined by:

$$\Delta t = 1.125 + 0.430T + 0.156t, \quad \text{(Eq. 3)}$$

Once again, where $\Delta t$ is the lag time in seconds, T is the hold temperature of the sample in degrees C. and t is the hold time in seconds at temperature T of the sample.

It has also been found that a target temperature $T_t$ of 55 degrees C. (131° F.) is acceptable for both sample integrity and comfortable sample handling. Accordingly, testing was carried out to determine the time lag or Δt between when the housing reached a target temperature $T_t$ of 55 degrees C. (131° F.) and the sample reached the target temperature $T_t$ of 55 degrees C. The time lag or Δt was found to be defined by:

$$\Delta t = (-8.12) + 0.130T + 0.00625t, \quad (Eq. 4)$$

where Δt is the lag time in seconds, T is the hold temperature of the sample in degrees C. and t is the hold time in seconds at temperature T of the sample for 1.00 inch and 1.25 inch diameter encapsulated samples; and $$\Delta t = (-29.0) + 0.367T + 0.0688t, \quad (Eq. 5)$$

where Δt is the lag time in seconds, T is the hold temperature of the sample in degrees C. and t is the hold time in seconds at temperature T of the sample for a 1.50 inch diameter encapsulated sample; and $$\Delta t = (-52.9) + 0.5430T + 0.162t, \quad (Eq. 6)$$

where Δt is the lag time in seconds, T is the hold temperature of the sample in degrees C. and t is the hold time in seconds at temperature T of the sample for a 2.0 inch diameter sample.

Accordingly, it has been found that for any target temperature $T_t$, the time lag or Δt between when the housing reaches the target temperature $T_t$ and when the sample reaches the target temperature $T_t$ can be determined experimentally by:

$$\Delta t = A + BT + Ct, \quad (Eq. 7)$$

where Δt is the lag time in seconds, T is the hold temperature of the sample in degrees C., t is the hold time in seconds at temperature T of the sample, and A, B and C are experimentally determined factors.

A method for making an encapsulated sample using an encapsulation system 10 in which a sample is encapsulated in a medium includes introducing a sample to be encapsulated and the encapsulating medium into a chamber 16. A temperature external of the chamber 16 is monitored by a sensor 64. In a present method, the temperature of the outer surface of the chamber housing 14 is monitored.

The sample and medium are then subjected to heat and pressure at a predetermined temperature and pressure for a predetermined period of time, the time being a hold time. Following the hold time, the encapsulated sample is cooled using a cooling fluid. In a present method, the cooling fluid is water that is circulated around the outer surface of the chamber, between the chamber and the chamber housing, and the temperature at an outer surface of the housing is monitored.

Upon reaching a predetermined temperature, the target temperature $T_t$, as monitored external of the chamber 16, a time lag (Δt) is established for a period of time to continue cooling fluid flow to cool the encapsulated sample. The time lag (Δt) is determined according to the formula:

Δt=A+BT+Ct, where Δt is the lag time in seconds, T is the hold temperature of the sample in degrees C., t is the hold time in seconds at temperature T of the sample, and A, B and C are experimentally determined factors.

For 1.00 inch and 1.25 inch diameter encapsulated samples and a target temperature $T_t$ of 40 degrees C., the time lag (Δt) is determined according to the equation Δt=6.73+0.0783T−0.0115t; for a 1.50 inch diameter encapsulated sample and a target temperature of 40 degrees C., the time lag (Δt) is determined according to the equation Δt=1.8+0.320T+0.604t; and for a 2.00 inch diameter encapsulated sample and a target temperature 40 degrees C., the time lag (Δt) is determined according to the equation Δt=1.125+0.430T+0.156t.

For 1.00 inch and 1.25 inch diameter encapsulated samples for a target temperature $T_t$ of 55 degrees C., the time lag (Δt) is determined according to the equation Δt=(−8.12)+0.130T+0.00625t; for a 1.50 inch diameter encapsulated sample and a target temperature $T_t$ of 55 degrees C., the time lag (Δt) is determined according to the equation Δt=(−29.0)+0.367T+0.0688t; and for a 2.00 inch diameter encapsulated sample and a target temperature $T_t$ of 55 degrees C., the time lag (Δt) is determined according to the equation Δt=(−52.9)+0.5430T+0.162t.

Thus, by knowing the size of the encapsulated sample, the temperature T at which it is held and time period t over which it is held at that temperature, and by remotely monitoring the temperature of the system 10, for example, at an outer surface of the chamber housing 14, and by applying certain parameters, the time Δt at which the encapsulated sample will reach a target temperature $T_t$ equal to the temperature of the outer surface of the housing, and at which the sample can be removed from the system 10 so as to maintain its integrity and to be comfortably handled can be determined.

Figure 12:
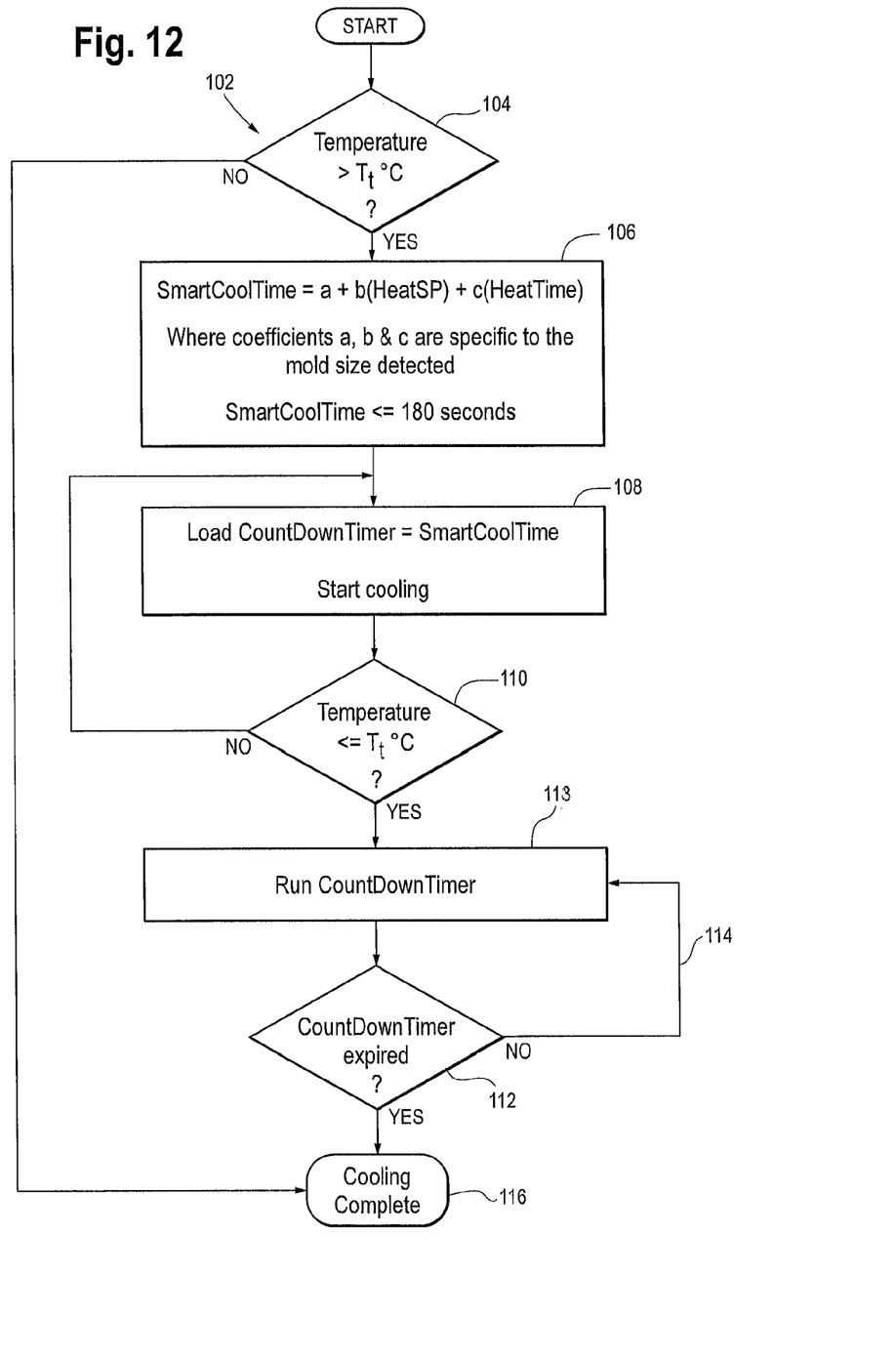
FIG. 12 is a flow diagram showing one embodiment of a control scheme for the cooling system for the sample encapsulation system.

Referring to FIG. 12, there is shown an embodiment of a cooling system operating scheme 102 for the sample encapsulation system. The operation of the cooling system 52 is integrated into the overall encapsulating system operating scheme and is controlled by the controller 20. The size of the encapsulated sample is input to the system through the control panel 22—again, this is done in conjunction with the overall operating scheme.

Following the encapsulation cycle, at block 104 the temperature at the remote location, presently at the outside of the chamber housing 16 is monitored. If the temperature is greater than the target temperature $T_t$ in degrees C., Δt is calculated by use of equation 7, based on the size of the encapsulated sample and the target temperature $T_t$, a countdown timer (equal to Δt) is set, and the cooling system is set to run for 180 seconds at blocks 106 and 108.

The temperature continues to be monitored at block 110 and if it is greater than the target temperature $T_t$, cooling continues. Once the temperature is monitored at less than the target temperature $T_t$, the countdown timer starts at block 113. If the countdown timer (Δt) has not expired, the cooling system continues to operate (line at 114). Once the countdown timer has expired (as block 112), cooling is complete and the cooling system stops at block 116.

Those skilled in the art will recognize the programming necessary to effectuate operation of the control system, and will appreciate the numerous other ways in which the system controls can operate.

All patents and patent applications referred to herein, are incorporated herein by reference, whether or not specifically done so within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present disclosure. It is to be understood that no limitation with respect to the specific embodiments illustrated is intended or should be inferred. The disclosure is intended to cover all such modifications as fall within its scope.

What is claimed is:

1. A sample encapsulation system comprising:
   a base;

a chamber, the chamber having an inlet;
a chamber housing in which the chamber is housed, the chamber fixedly mounted at least in part within the chamber housing, the chamber housing movably mounted to the base;
a cap;
a first ram operably mounted to the cap for engaging the chamber inlet;
a second ram positioned in the chamber opposite the inlet, the second ram movable toward and away from the first ram,
wherein the chamber and chamber housing are movable toward the cap for engaging the first ram with the chamber inlet during an encapsulation cycle and away from the cap, disengaging the first ram from the chamber inlet following an encapsulation cycle.

2. The sample encapsulation system of claim 1 wherein the cap is formed as part of a cap assembly, and wherein the cap assembly includes a mounting plate, and wherein the cap secures to mounting plate.

3. The sample encapsulation system of claim 2 wherein the mounting plate is stationary relative to the chamber housing and chamber and wherein when the cap is secured to the mounting plate, the chamber and chamber housing are movable toward the mounting plate for the first ram to engage the chamber inlet and the chamber and chamber housing are movable away from the mounting plate to disengage the first ram from the chamber inlet.

4. The sample encapsulation system of claim 2 wherein the cap is movable toward and away from the mounting plate, and wherein the cap is lockable to the mounting plate when in the encapsulation cycle.

5. The sample encapsulation system of claim 4 wherein the cap is movable toward and away from the mounting plate along a post.

6. The sample encapsulation system of claim 5 including a constant force spring operably connected to the cap for moving the cap toward and away from the mounting plate.

7. The sample encapsulation system of claim 1 wherein the chamber has a tapered wall section at about the inlet, the tapered wall section expanding outwardly toward the inlet.

8. The sample encapsulation system of claim 7 wherein the first ram has a tapered profile for mating with the chamber inlet tapered wall.

9. The sample encapsulation system of claim 8 wherein the chamber inlet has a two-step tapered wall section, a first tapered wall section at the inlet, transitioning to a relatively straight-walled section, the straight walled section transitioning to a second tapered wall section.

10. The sample encapsulation system of claim 9 wherein the first ram has a tapered wall for mating with the chamber second tapered wall section during the encapsulation cycle and for disengaging from the second tapered wall section following the encapsulation cycle.

11. The sample encapsulation system of claim 1 wherein the chamber and/or chamber housing includes an inwardly oriented lip at a lower end thereof, and wherein the second ram engages the inwardly oriented lip following the encapsulation cycle to move the chamber and chamber housing away from the cap and disengaging the chamber inlet from the first ram, and wherein disengagement of the second ram from the inwardly oriented lip permits movement of the chamber housing and chamber toward the cap for engaging the chamber inlet with the first ram.

12. A sample encapsulation system comprising:
a base;
a chamber;
a chamber housing in which the chamber is housed, the chamber fixedly mounted at least in part within the chamber housing, the chamber housing movably mounted to the base for movement toward and away from the base;
a cap;
a heating assembly and a cooling assembly, the heating assembly and the cooling assembly disposed about the chamber; and
a temperature sensor mounted remotely from an interior of the chamber.

13. The sample encapsulation system of claim 12 wherein the temperature sensor is mounted to the chamber housing remote from an encapsulated sample within the chamber and wherein the remote sensed temperature is used to continue or stop operation of the cooling system following a predetermined period of time after the remote sensed temperature reaches a set point temperature based upon a predicted temperature of the encapsulated sample as determined by the remote sensed temperature.

14. The sample encapsulation system of claim 13 including means for determining the predetermined period of time of cooling system operation.

15. The sample encapsulation system of claim 14 wherein the predetermined period of time is a time lag ($\Delta t$), and wherein $\Delta t$ for an encapsulated sample having a predetermined diameter is determined according to the formula $\Delta t = A + BT + Ct$, where T is a hold temperature of the encapsulated sample in degrees C., t is a hold time in seconds at the hold temperature of the encapsulated sample and where A, B and C are experimentally determined factors based upon the set point temperature.

16. The sample encapsulation system of claim 15 wherein
for an encapsulated sample having a 1.0 to 1.25 inch diameter and a set point temperature of 40 degrees C., A is 6.73, B is 0.0783 and C is −0.0115 or at a set point temperature of 55 degrees C. A is −8.12, B is 0.130 and C is 0.00625t, or
for an encapsulated sample having a 1.5 inch diameter and a set point temperature of 40 degrees C., A is 1.8, B is 0.320 and C is 0.604, or at a set point temperature of 55 degrees C., A is −29.0, C B is 0.367 and C is +0.0688t, or
for an encapsulated sample having a 2.0 inch diameter and a set point temperature 40 degrees C., A is 1.125, B is 0.430T and C is 0.156t, or at a set point temperature of 55 degrees C., A is −52.9, B is 0.543 and C is 0.162.

17. The sample encapsulation system of claim 13 including means for establishing the set point temperature, means for determining the lag time ($\Delta t$) for cooling fluid flow and means for stopping fluid cooling flow after the set point temperature has been reached and the lag time has expired.

18. The sample encapsulation system of claim 17 wherein the means for determining the lag time ($\Delta t$) for cooling fluid flow is based, at least in part, on a size of the sample and the set point temperature.

19. The sample encapsulation system of claim 17 wherein the means for determining the lag time ($\Delta t$) for cooling fluid flow is based, at least in part, on a diameter of the sample.

20. A sample encapsulation system comprising:
a base;
a chamber, the chamber having an inlet;
a chamber housing in which the chamber is housed, the chamber fixedly mounted at least in part within the chamber housing, the chamber housing movably mounted to the base, one or both of the chamber and chamber housing including an inwardly oriented lip at a lower end thereof;

a cap;

a first ram operably mounted to the cap for engaging the chamber inlet;

a second ram positioned in the chamber opposite the inlet, the second ram movable toward and away from the first ram;

a heating assembly and a cooling assembly, the heating assembly and the cooling assembly disposed about the chamber; and a temperature sensor mounted remotely from an interior of the chamber, wherein the second ram engages the inwardly oriented lip following the encapsulation cycle to move the chamber and chamber housing away from the cap and disengaging the chamber inlet from the first ram, and wherein disengagement of the second ram from the inwardly oriented lip permits movement of the chamber housing and chamber toward the cap for engaging the chamber inlet with the first ram, and wherein the temperature sensor senses a temperature remote from an encapsulated sample within the chamber and wherein the remote sensed temperature is used to continue or stop operation of the cooling system based upon a predicted temperature of the encapsulated sample as determined by the remote sensed temperature.

* * * * *